US006098618A

United States Patent [19]
Jennings et al.

[11] Patent Number: 6,098,618
[45] Date of Patent: Aug. 8, 2000

[54] INHALATION DEVICE

[75] Inventors: Douglas Jennings, Herts, United Kingdom; Magnus Jeppsson, Lund, Sweden

[73] Assignee: Astra Aktiebolag, Sodertalje, Sweden

[21] Appl. No.: 09/066,336

[22] PCT Filed: Mar. 13, 1998

[86] PCT No.: PCT/SE98/00464

§ 371 Date: Apr. 27, 1998

§ 102(e) Date: Apr. 27, 1998

[87] PCT Pub. No.: WO98/41263

PCT Pub. Date: Sep. 24, 1998

[30] Foreign Application Priority Data

Mar. 14, 1997 [SE] Sweden .................................. 9700936

[51] Int. Cl.[7] ..................................................... A61M 15/00

[52] U.S. Cl. ................................ 128/203.15; 128/203.14

[58] Field of Search ......................... 128/203.15, 203.14, 128/203.21, 203.23, 200.14, 200.23; 222/162, 634

[56] References Cited

U.S. PATENT DOCUMENTS

| | | | |
|---|---|---|---|
| 2,470,296 | 5/1949 | Fields | 128/266 |
| 2,573,918 | 11/1951 | McCuiston | 128/206 |
| 3,858,583 | 1/1975 | Hallworth et al. . | |
| 3,948,264 | 4/1976 | Wilke et al. | 128/266 |
| 4,524,769 | 6/1985 | Wetterlin | 128/203.15 |
| 4,739,754 | 4/1988 | Shaner . | |
| 5,082,148 | 1/1992 | Dunning | 222/162 |
| 5,372,128 | 12/1994 | Haber et al. | 128/203.21 |
| 5,437,271 | 8/1995 | Hodson et al. | 128/203.15 |
| 5,522,383 | 6/1996 | Calvert et al. | 128/203.15 |
| 5,694,920 | 12/1997 | Abrams et al. | 128/200.16 |
| 5,758,637 | 6/1998 | Ivri et al. | 128/200.14 |

FOREIGN PATENT DOCUMENTS

| | | | |
|---|---|---|---|
| 24211 | 3/1993 | Australia . | |
| 0069715 | 6/1982 | European Pat. Off. . | |
| 0 215 559 A1 | 7/1986 | European Pat. Off. . | |
| 0237507 | 2/1987 | European Pat. Off. . | |
| 0 705 614 A1 | 4/1990 | European Pat. Off. . | |
| 0 424 790 A2 | 5/1991 | European Pat. Off. . | |
| 0 640 354 A1 | 9/1991 | European Pat. Off. . | |
| 0 573 128 A2 | 11/1991 | European Pat. Off. . | |
| 0 520 440 A1 | 6/1992 | European Pat. Off. . | |
| 0 634 184 A1 | 1/1995 | European Pat. Off. . | |
| 0 703 159 A1 | 9/1995 | European Pat. Off. . | |
| 1 295 081 | 11/1972 | United Kingdom . | |
| 1565029 | 11/1977 | United Kingdom | 83/14 |
| WO 90/13328 | 11/1990 | WIPO . | |
| WO 92/04066 A1 | 3/1992 | WIPO . | |
| WO 92/04068 A1 | 3/1992 | WIPO . | |
| WO 93/03782 | 3/1993 | WIPO . | |
| WO 94/11044 A2 | 5/1994 | WIPO . | |
| WO 94/13348 | 6/1994 | WIPO . | |
| WO 94/14492 | 7/1994 | WIPO . | |
| WO 95/24234 | 9/1995 | WIPO . | |

OTHER PUBLICATIONS

International Search Report.

*Primary Examiner*—Aaron J. Lewis
*Assistant Examiner*—Teena Mitchell
*Attorney, Agent, or Firm*—Fish & Richardson P.C.

[57] ABSTRACT

An inhalation device for providing a substance in a dispersed state, comprising internal surfaces for ducting the substance and containing the same in a dispersed state and a mechanism for creating vibrations in at least some of the internal surfaces.

22 Claims, 10 Drawing Sheets

INHALATION DEVICE

This is a continuation of International Patent Application No. PCT/SE98/00464, with an international filing date of Mar. 13, 1998, now pending.

BACKGROUND

The present invention relates to an inhalation device for providing a substance in a dispersed state.

Inhalable pharmaceutically active substances are generally used for the treatment of diseases in the bronchial and pulmonary areas, such as asthma and chronic bronchitis. Various kinds of inhalation devices are used for this purpose.

One kind of inhalation device is the breath-actuated inhaler, particularly but not necessarily a dry powder inhaler, which contains multiple doses of powder containing an active substance. One such inhaler is the Turbuhaler® dry powder inhaler. Such an inhaler has a rotatable grip portion for providing a dose of powder for inhalation. Inhalers of this kind are disclosed in EP-A-0069715 and EP-A-0237507.

SUMMARY OF THE INVENTION

The operation of this inhaler relies on the creation of an air flow resulting from inhalation by a user. The air flow draws up the powder containing active substance and disperses the same therewithin. Deagglomeration of agglomerates must also be achieved during inhalation; agglomerates always occurring in fine powders, especially finely divided powders of the kind suitable for inhalation.

Some patients such as small children and the elderly with bronchial diseases are, however, not able to use breath-actuated inhalers as these patients cannot develop the necessary inhalation flow rates, typically about 30–60 l/min. These patients have to use pressurised metered dose inhalers which use a propellant such as freon (CFC). Such inhalers suffer from many known disadvantages, particularly undesirable side effects both for the environment and the patients.

In order to facilitate the inhalation of pharmaceutically active substances which are delivered by the use of pressurised metered dose inhalers, it is known to use dispersion chambers of considerable volume, typically up to 2000 ml, into which the substance entrained in the pressurised gas is dispersed. These devices are generally known as spacers. GB-A-1565029 discloses a typical spacer.

Inhalation devices which include dispersion chambers have also been developed for dry-powder inhalers of the above-mentioned kind. One such an inhalation device is disclosed in EP-A-0548152. This device comprises a reservoir of powder containing active substance (which reservoir can be part of a dry powder inhaler disposed within the inhalation device) and a dispersion chamber. The dispersion chamber has a movable wall which varies the volume of the dispersion chamber between minimum and maximum volumes so as to draw powder containing active substance into the dispersion chamber. The movable wall is provided as a piston which when moved creates a negative pressure within the dispersion chamber. When dispersed, a patient can then inhale the powder containing active substance through a face mask or mouthpiece.

It is an aim of the present invention to ensure that powder containing active substance does not accumulate on internal surfaces of the inhalation device.

According to the present invention there is provided an inhalation device for providing a substance in a dispersed state, comprising: internal surfaces for ducting said substance and for containing said substance in a dispersed state; and a mechanism for creating vibrations in at least some of said internal surfaces so as to ensure that substance does not accumulate on the at least some of the internal surfaces.

According to the present invention there is also provided a method of ensuring that substance does not accumulate on internal surfaces of an inhalation device for providing said substance in a dispersed state, the method comprising the step of: creating vibrations in at least some of the internal surfaces so as to dislodge substance therefrom.

In this way, any small amounts of substance which deposit on the internal surfaces are dislodged into the air within the inhalation channel. Preferably, the vibrations are caused immediately prior to use, such that the dislodged substance is carried away, thereby minimizing the possibility of retention of substance.

Preferably, the vibrations are caused by the release of a sprung component which impacts a wall of the inhalation device. Of course, other mechanisms, including electrical systems, could be used, but these tend to be more complicated.

Preferably, the inhalation device includes a component, such as the dispersion chamber and/or mouthpiece, movable between a storage position and an operative position, the mechanism being linked to the component so as to create vibrations when the component is moved between the storage position and the operative position.

In this way, substance is automatically dislodged from internal surfaces of the inhalation device without any special action on the part of the user.

Preferably, the component has an opening, such as the opening of the mouthpiece, into which a hook portion may be inserted. The hook portion may be linked to the mechanism to move the same against the bias of a spring such that when the hook releases from the opening, the mechanism returns, under the force of the spring, to impact with a surface of the inhalation device.

Thus, vibrations may be automatically and assuredly induced in the inhaler using a mechanism which is relatively straightforward to construct. Furthermore, the use of an opening such as the opening of the mouthpiece avoids the need for any special components to operate the mechanism.

A preferred embodiment of the present invention will now be described hereinbelow by way of example only with reference to the accompanying drawings.

BRIEF DESCRIPTION OF THE DRAWINGS

FIG. 1 illustrates a vertical sectional side view of an inhalation device in accordance with a preferred embodiment of the present invention, illustrated in the storage position;

FIG. 2 illustrates a vertical sectional view of the device of FIG. 1 in the retracted but non-activated position;

FIG. 3 illustrates a vertical sectional view of the device of FIG. 1 in activated position;

FIG. 4 illustrates a vertical sectional view of the device of FIG. 1 in activated position, with the flow of air being illustrated schematically;

FIG. 5 illustrates a vertical sectional view of the device of FIG. 1 incorporating a preferred mouthpiece valve, illustrated in the retracted position;

FIGS. 6(*a*) to 6(*c*) illustrate component parts of another mouthpiece valve;

DETAILED DESCRIPTION OF THE PREFERRED EMBODIMENTS

The inhalation device also referred to as a spacer herein, comprises a housing 1 containing a first chamber 2, which defines a suction chamber of variable volume, and a second, dispersion chamber 3 of constant volume. In this embodiment the chambers 2, 3 are cylindrical, but any other form is possible. The chambers 2, 3 are axially telescopically movable in relation to each other and a fluid connection is provided therebetween.

Figure 1:
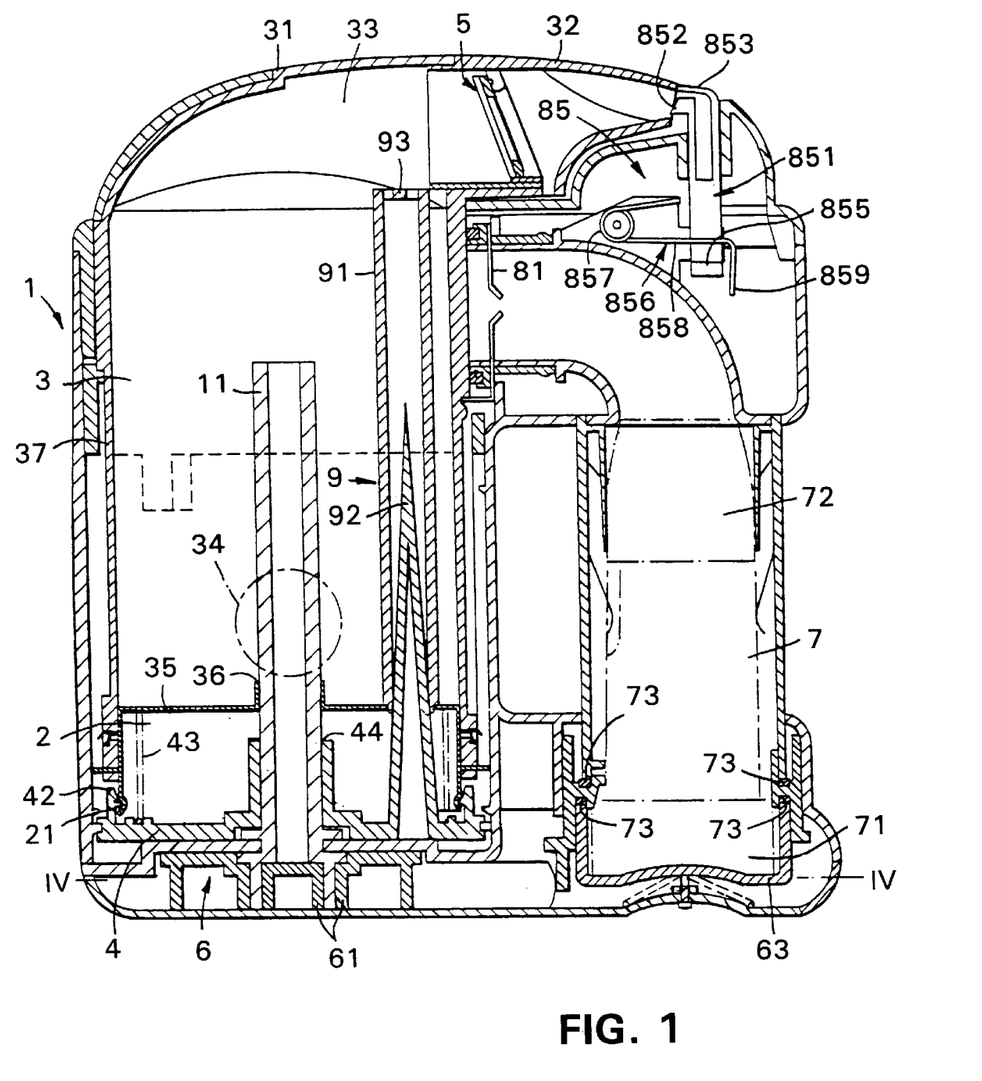
Figure 3:
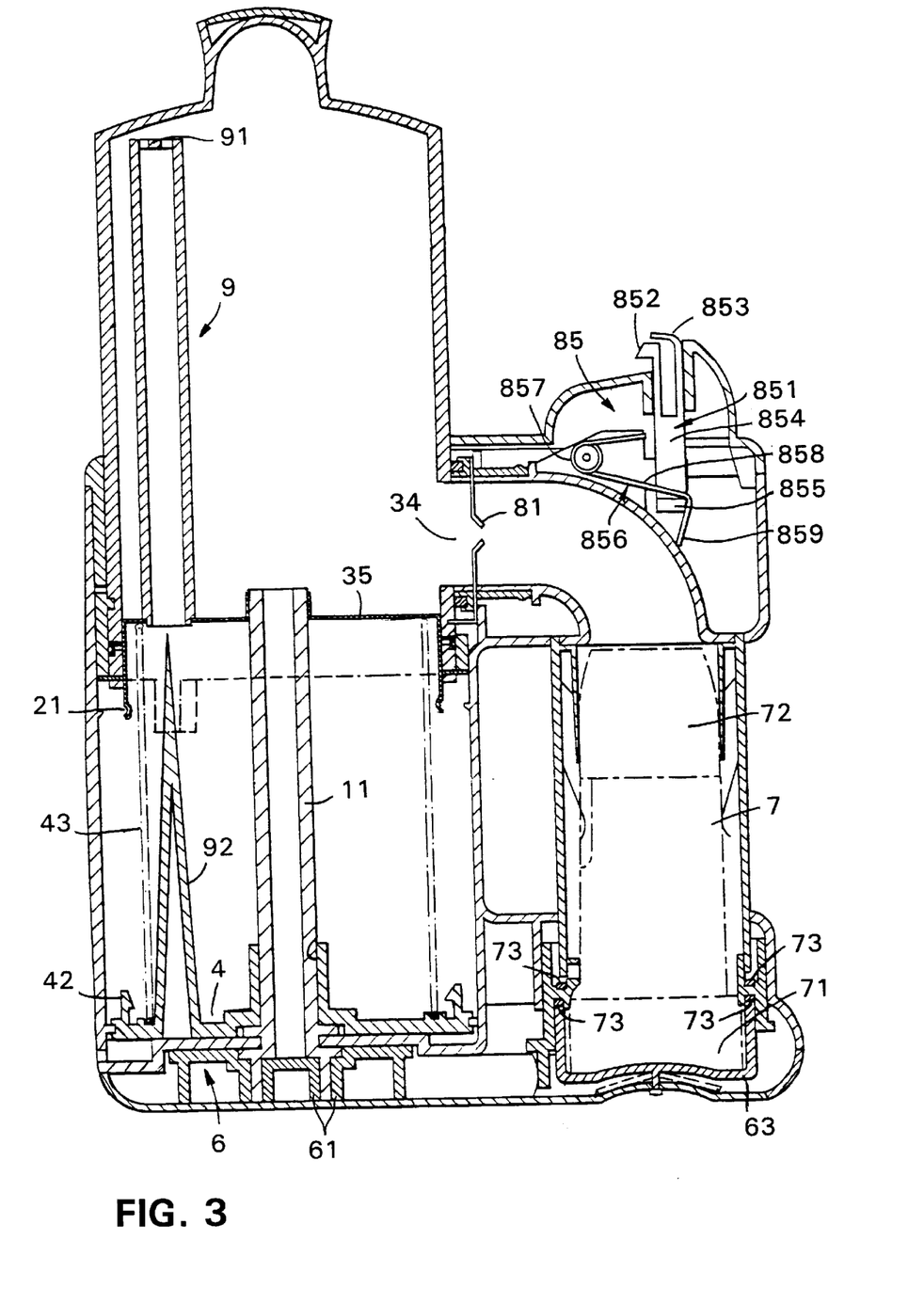
Figure 4:
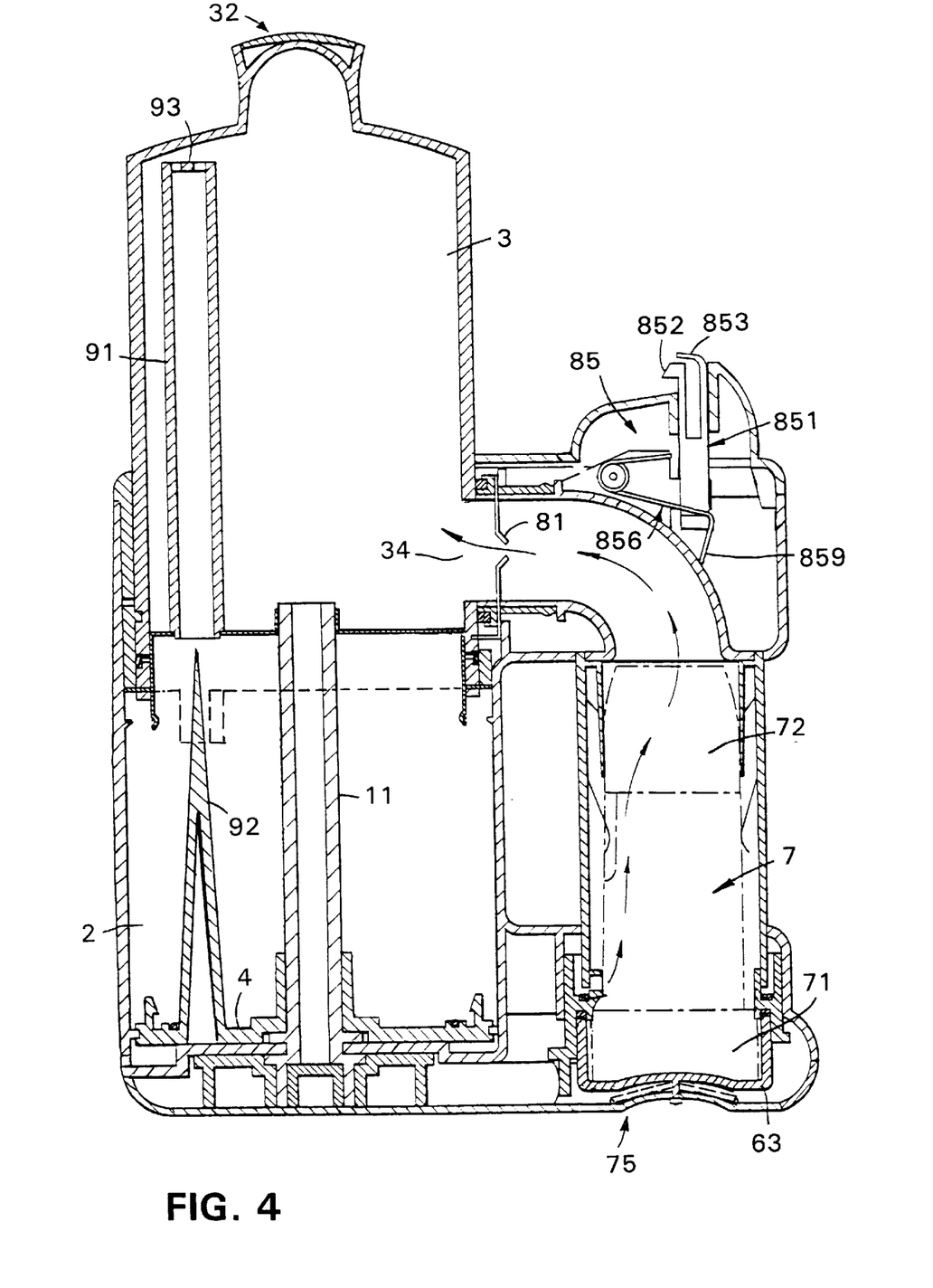

The dispersion chamber 3 includes a lid 31 which covers the upper part thereof. The lid 31 may be a separate component or formed integrally with the dispersion chamber 3. The lid 31 includes a mouthpiece 32 which is taken in the mouth of a user when the device is to be used. The mouthpiece 32 is preferably detachable from the lid 31, for instance by means of a bayonet fitting. In this way, the mouthpiece 32 may be removed for cleaning. Inside the lid 31, an inhalation channel 33 is arranged between and in fluid connection with the dispersion chamber 3 and the mouth piece 32. When the device is to be used, the dispersion chamber 3 is moved from the retracted position as illustrated in FIG. 1 and an activated position as illustrated in FIG. 3. If the user is a small child a face mask of any known kind can be mounted to the mouthpiece 32 or the mouthpiece 32 can be exchanged for such a face mask.

Figure 5:
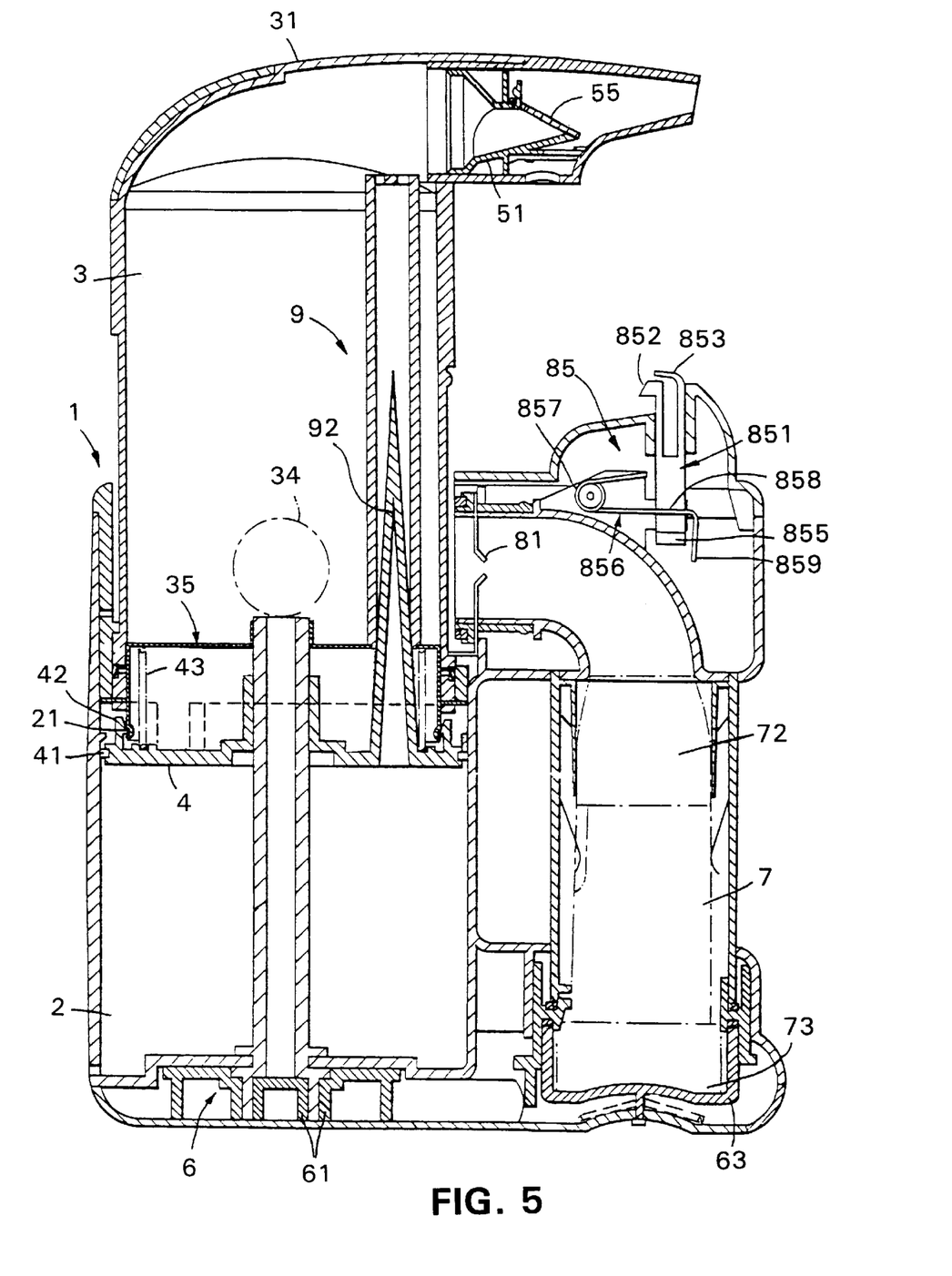
Figure 6A:
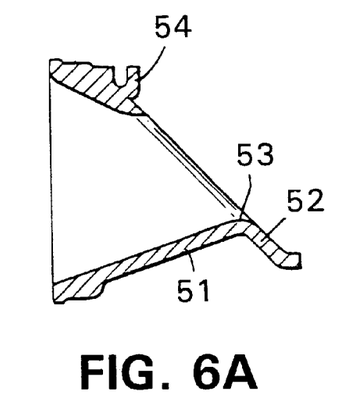
Figure 6B:
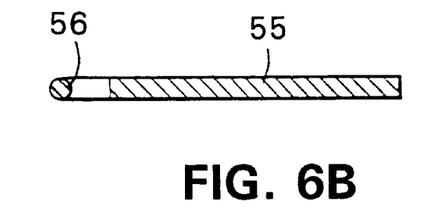
Figure 6C:
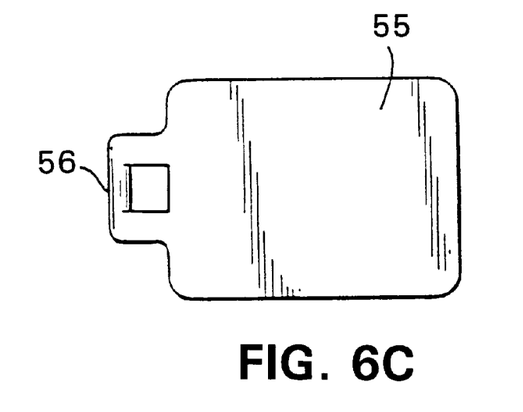

A one-way valve 5 is provided in the inhalation channel 33. When the device is in use and a user inhales through the mouthpiece 32, the valve 5 opens to let inhales air pass therethrough into the mouth of the user. When the user exhales, the valve 5 closes to prevent exhaled air from passing through the inhalation channel 33 and into the dispersion chamber 3. In this embodiment the valve 5 is a flap valve. FIG. 5 illustrates the device with a preferred mouthpiece valve 5. FIGS. 6(a) to 6(c) illustrate the component parts of another mouthpiece valve 5. The valve 5 comprises an insert 51 having a valve seat 52, an aperture 53 and a bearing 54, and a flap 55. The valve flap 55, as illustrated in FIGS. 6(*b*) and 6(*c*), includes a shaft 56 for insertion into the bearing 54 such that the flap 55 may freely rotate about the bearing 54. In the valve 5 illustrated in FIG. 6, when the insert 51 is fitted in the mouthpiece 32, the wall of the mouthpiece 32 closes the bearing 54.

The device further comprises mounting and activating means 6 for mounting and activating an inhaler 7 which may be an internal part of or detachably mounted to the housing 1. In this embodiment the inhaler 7 is a Turbuhaler® dry powder inhaler and is disposed in a cavity adjacent first chamber 2. The inhaler 7 comprises an inhalation channel, a storage chamber containing powder to be inhaled, a dosing unit for providing a dose of powder to the inhalation channel, a rotatable grip portion 71 for operating the dosing unit and a mouthpiece 72 through which a user inhales. Although in this embodiment the device is configured to receive a Turbuhaler® dry powder inhaler, it will be appreciated that any other inhaler of this or a similar kind could be employed. The mounting and activating means 6 will be described in more detail hereinbelow.

When the inhaler 7 is mounted in the housing 1, the mouthpiece 72 of the inhaler 7 is connected to the dispersion chamber 3 via a first end of a substantially L-shaped channel 8. The other end of the channel 8 is arranged to be in fluid connection with the dispersion chamber 3 via an opening 34 provided in the peripheral wall 37 thereof when the dispersion chamber 3 is in the retracted and rotated, that is activated, position. A seal 81 is provided to the other end of the channel 8 such that when the device is in the retracted position the opening 34 is located remote from the channel 8 and an air tight seal is established between the inhaler 7 and the dispersion chamber 3.

Many pharmaceutically active substances are hydroscopic. In being sensitive to humidity these substances must be kept in an environment with a stable humidity. In order to prevent the inhaler 7 from being unnecessarily exposed to moisture the cavity in which the inhaler 7 is located is sealed from the atmosphere in an air tight manner when the device is in the storage position. This seal is only broken when the device is activated for inhalation, that is, when the dispersion chamber 3 is rotated to the activated position. When in the activated position, an inlet 75 in a wall adjacent the first chamber 2 is opened through which air can be drawn. After use, the dispersion chamber 3 is rotated and returned to the collapsed position, with the inlet 75 being closed and an air tight seal achieved again.

As mentioned hereinabove, the first chamber 2 and the dispersion chamber 3 are telescopically movable in relation to each other. Guiding elements are preferably provided which guide the movement of the chambers 2, 3 in relation to each other. These guiding elements can be provided as a pin on the surface of one of the chambers 2, 3 and a corresponding groove provided on the surface of the other of the chambers 2, 3. The function of the guiding elements will be further described hereinbelow in relation to the operation of the device.

The dispersion chamber 3 is disposed within the first chamber 2 such that the bottom wall 35 thereof defines the top wall of the first chamber 2. The first chamber 2 includes a piston 4 disposed therewithin which is movable between a retracted, first position and a released, second position as illustrated in FIGS. 2 and 3 respectively. The piston 4, the bottom wall 35 and the peripheral wall of the first chamber 2 together define a suction chamber, the volume of which is altered by movement of the piston 4. The piston 4 includes a peripheral seal 41 for providing an air tight seal against the peripheral wall of the first chamber 2 during most of the travel of the piston 4. The first chamber 2 further includes a biasing means 43 disposed therewithin between the bottom wall 35 of the dispersion chamber 3 and the piston 4; the biasing means 43 being provided to drive the piston 4 to the released position when the piston 4 is released from the retracted position. The biasing means 43 is preferably a compression spring. The piston 4 includes lugs 42 which latch into grooves 21 provided on the bottom of the dispersion chamber 3, thereby holding the piston 4 against the biasing force of the biasing means 43 and locking the same in the retracted position.

The device further comprises a flow regulating device 9 in fluid communication with the dispersion chamber 3 for achieving an optimum flow profile for the air drawn through the inhaler 7, where the flow rate increases in a controlled manner to a maximum rate of about 60 l/min. This flow regulating device 9 compensates for the characteristics of the sprung components, that is, the piston 4 and the biasing means 43 described hereinabove. In this embodiment the flow regulating device 9 is constructed as a flow regulating valve and is operably attached to the piston 4. The flow regulating valve 9 is formed as a needle valve comprising a stand pipe 91 and a cone-shaped needle 92 movably disposed within the stand pipe 91. The stand pipe 91 is mounted to the bottom wall 35 of the dispersion chamber 3 and extends upwardly inside the dispersion chamber 3. A one-way valve 93 is disposed in the upper part of the stand pipe 91 allowing fluid, which is air or even gas, to enter into the stand pipe 91 and down into the variable volume of the suction chamber. The needle 92 is mounted to the piston 4 and protrudes upwardly into the stand pipe 91. In the retracted position of the piston 4, substantially the entire length of the needle 92 is disposed within the stand pipe 91. When the piston 4 is released from the retracted position and moves downwardly so as to increase the volume of the suction chamber, the needle 92 moves with the piston 4 and out of the stand pipe 91. The needle 92 restricts the cross section of the stand pipe 91 and thereby restricts the valve clearance in the stand pipe 91. The air flow down through the stand pipe 91 is thus most restricted at the point of release of the piston 4, but this restriction will decrease as the needle 92 moves downwardly out of the stand pipe 91 and into the first chamber 2. For optimal performance the air flow profile should be the same every time the device is used. This is achieved by the arrangement of the stand pipe 91 and the needle 92. With the above-described construction, the speed, force and air flow profile of the air flow through the device is optimised. The shape and length of the needle 92 is such as to achieve an optimised inhalation air flow. Of course, other forms and shapes of the needle 92 and the standpipe 91 could be used, provided that the requirements of flow restriction are met.

The mounting and activating means 6 mentioned hereinabove comprises a shaft 1, having a square or rectangular cross section, which is mounted to the bottom wall of the housing 1 and protrudes into the first chamber 2 and the dispersion chambers 3 through holes 44, 36 in the piston 4 and the bottom wall 35 of the dispersion chamber 3 respectively.

Figure 7A:
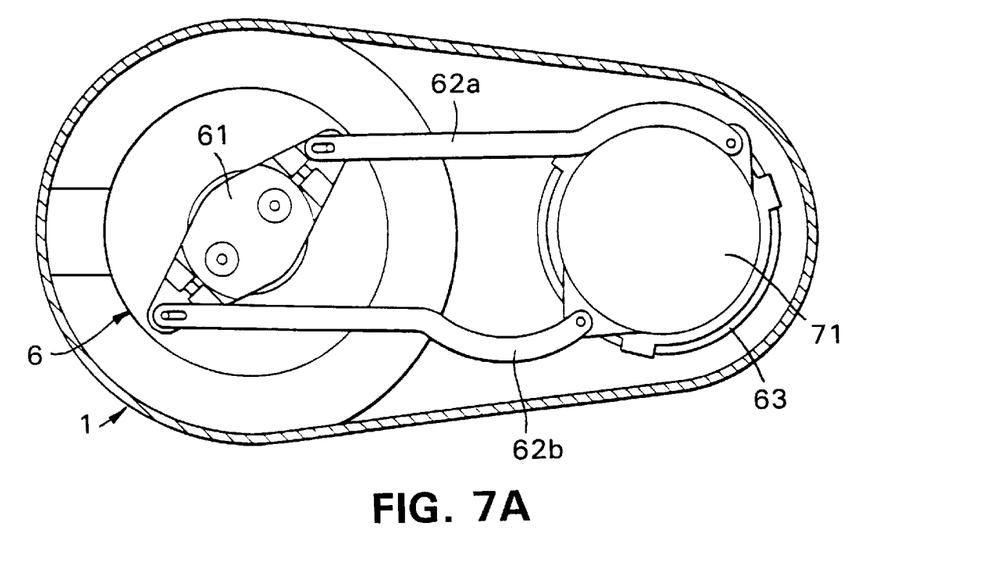
FIG. 7(a) illustrates a horizontal sectional view (along section IV—IV in FIG. 1) of the device of FIG. 1, illustrated in the storage position.
Figure 7B:
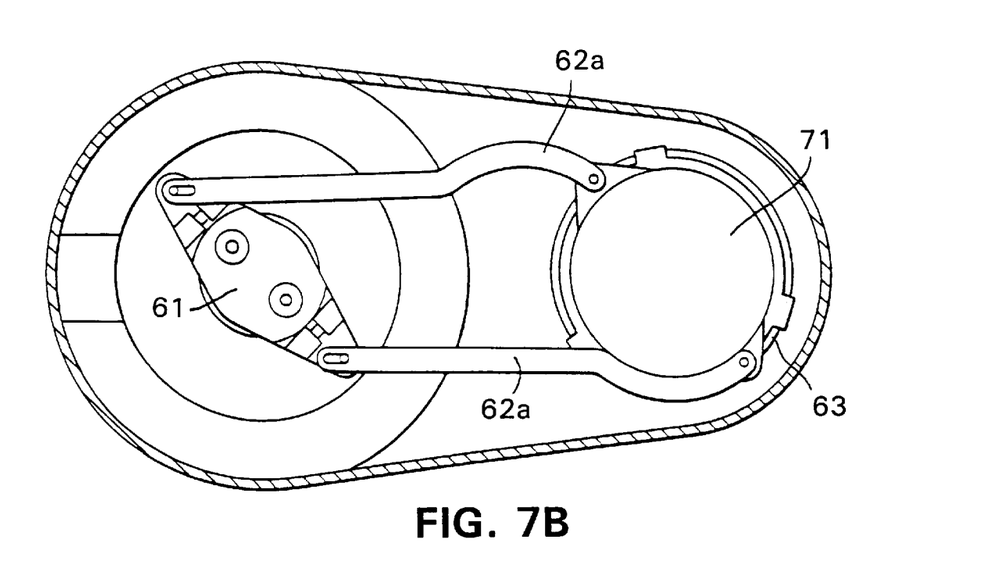
FIG. 7(b) illustrates a horizontal sectional view (along section IV—IV in FIG. 1) of the device in FIG. 1, illustrated in the activated position.

In one embodiment, a lever 61 is connected to the lower end of the shaft 11. As illustrated in FIGS. 7(a) and 7(b), at least one, preferably two further levers 62a, 62b are connected at one end to the first lever 61. The other ends of the further levers 62a, 62b are connected to a mounting element 63 in which the rotatable grip portion 71 of the inhaler 7 is located. The further levers 62a, 62b are connected to the mounting element 63 in such a manner that movement thereof causes the mounting element 63 to rotate, whereby the grip portion 71 of the inhaler 7 is also rotated. The rotation of the grip portion 71 corresponds to the required movement of the dosing unit for providing a dose of powder to the inhalation channel of the inhaler. The length and form of the further levers 62a, 62b is determined by the required rotational movement of the grip portion 71.

Figure 8:
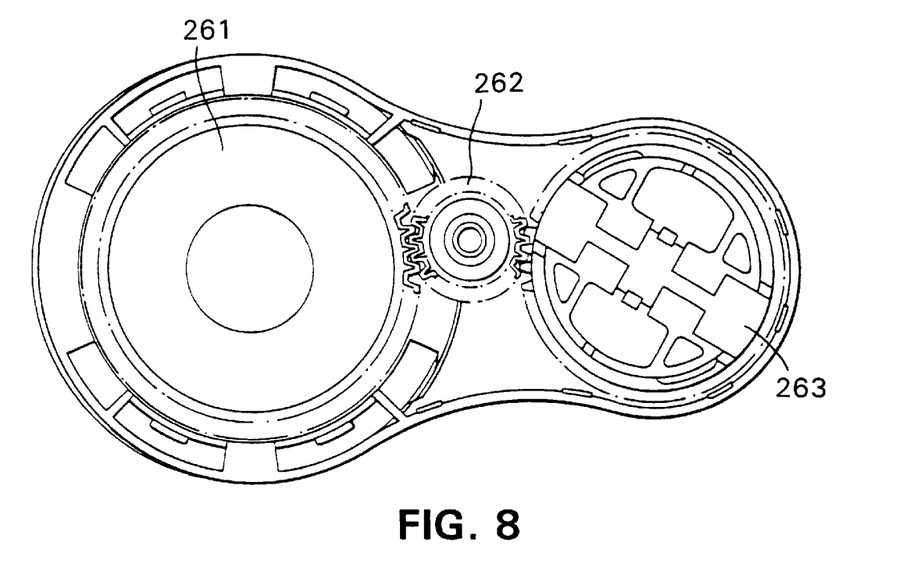
FIG. 8 illustrates an alternative linkage for the mounting element of the device of FIG. 1.

In alternative embodiment, as illustrated in FIG. 8, a first gear 261 is connected to the lower end of the shaft 11. The first gear 261 is connected via an intermediate gear 262 to a mounting gear 263 which is attached to the mounting element 63.

The operation of the device will now be described hereinbelow.

Initially, the device is in the storage position as illustrated in FIG. 1, with the dispersion chamber 3 located in the first chamber 2 and the mouthpiece 32 adjacent the housing 1. When required, the dispersion chamber 3 is retracted, that is, raised in relation to the first chamber 2, as illustrated in FIG. 1. Thereafter, the mouthpiece 32 is rotated through an angle of about 90° to the activated position. In this embodiment the mouthpiece 32 is mounted to or formed as a part of the lid 31 which is rigidly connected to or formed as a part of the dispersion chamber 3. Movement of the mouthpiece 32 thus releases the piston 4 from the locked position. In this embodiment the dispersion chamber 3 is rotated through an angle of about 90° in a horizontal plane, as illustrated in the FIGS., but the required angle of rotation can be made less or more than 90° simply by modifying the arrangement of the lever arms or the number of gear teeth in the mounting and activating means 6. This is because the rotating movement of the grip portion 71 to provide a dose to the inhalation channel determines the required movement of the mounting element 63. The mounting element 63 is rotated by movement of the lever arms 61, 62a and 62b or the gears 261, 262, 263 when the device is activated, that is, when the dispersion chamber 3 and the mouthpiece 32 are rotated.

When the lid 31 and the mouthpiece 32 are rotated to activate the device, the movement of the dispersion chamber 3 and the piston 4 is transferred to the first lever 61 or gear 261 via the shaft 11. The first lever 61 rotates and transfers this movement to the further levers 62a and 62b and the first gear 261 transfers this movement to the further gears 262, 263, which levers or gears then rotate the mounting element 63 and the grip portion 71 of the inhaler 7.

As described hereinabove, the mounting and activating means 6 of the inhaler 7 is arranged in such manner that the grip portion 71 of the inhaler 7 is rotated when the mouthpiece 32 is rotated to the activated position. In this way, a dose of powder to be inhaled is provided to the inhalation channel of the inhaler 7.

In the initial retracted position, the lugs 42 on the piston 4 are latched in the locked position in the grooves 21 in the bottom wall 35 of the dispersion chamber 3. When the dispersion chamber 3 is raised in relation to the first chamber 2, the piston 4 follows the dispersion chamber 3 upwardly until an end position is reached. When the end position is reached, the mouthpiece 32 is rotated and the guiding elements disposed between the chambers 2, 3 cause the lugs 42 to be released such that the piston 4 is released. Owing to the biasing force of the biasing means 43, the piston 4 is driven downwardly away from the wall 35 inside the first chamber 2, thereby increasing instantly the volume of the suction chamber. Air is drawn through the stand pipe 91 from the dispersion chamber 3 down into the suction chamber and a negative pressure or vacuum is created in the dispersion chamber 3. As mentioned hereinabove, an air inlet 75 is provided in the bottom wall of the housing 1 through which air is drawn into the cavity in which the inhaler 7 is housed. By the provision of a seal 73 around the periphery of the inhaler 7, the only path for the air is through the inhalation channel of the inhaler 7. Thus, the dose of powder which has already been located in the inhalation channel of the inhaler 7 is drawn up and mixed with the air in the air flow. This air containing powder is drawn up through the mouthpiece 72 of the inhaler 7 via the channel 8 into the dispersion chamber 3 through the opening 34.

In this embodiment the stand pipe 91 is constructed in such a manner that the volume of air passing down to the suction chamber is less then the volume of the dispersion chamber 3. In this manner, no appreciable amount of powder will enter the stand pipe 91.

Figure 9:
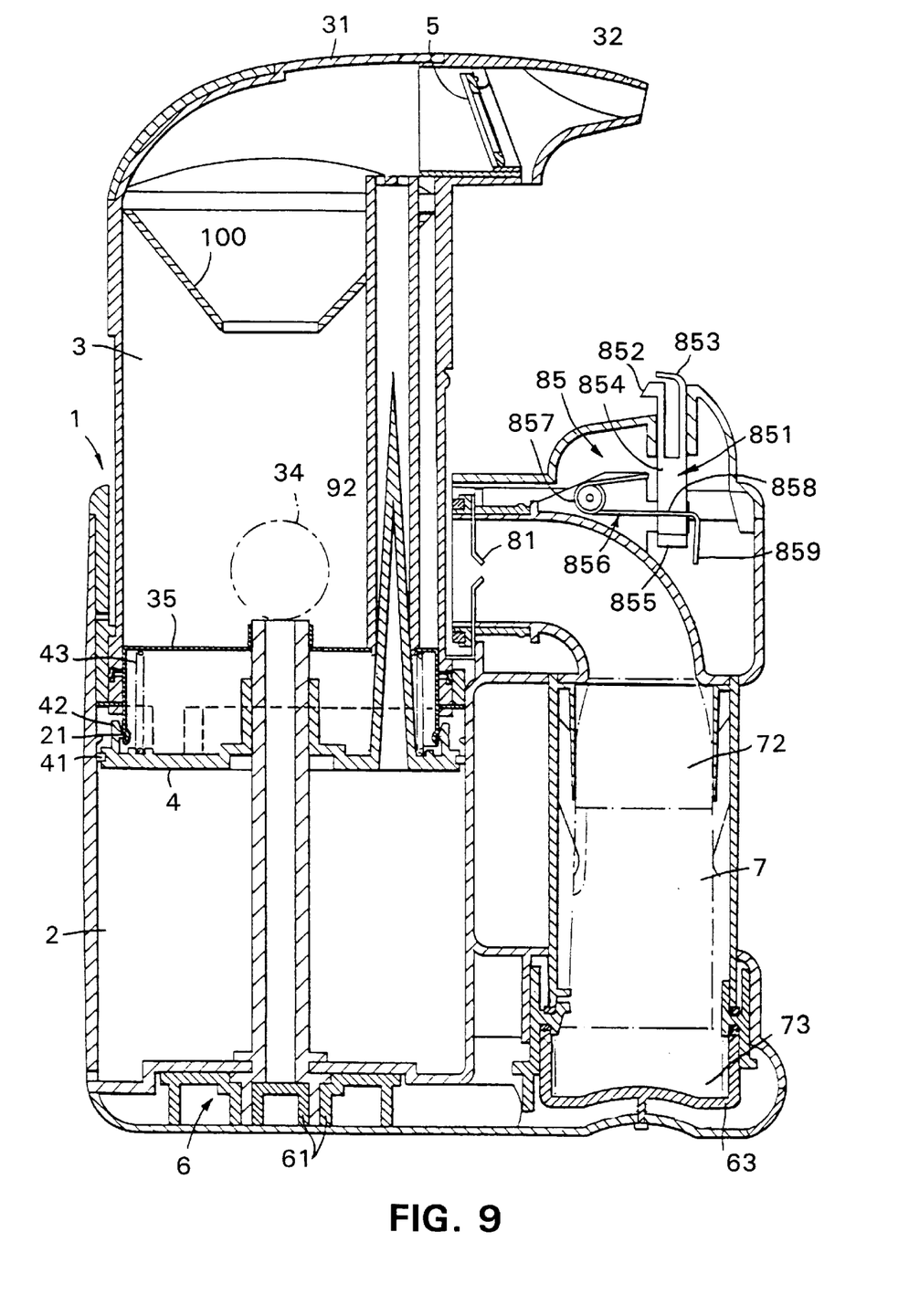
FIG. 9 illustrates a vertical sectional view of the device of FIG. 1 incorporating an insert in the dispersion chamber for preventing the escape of collected powder.
Figure 10A:
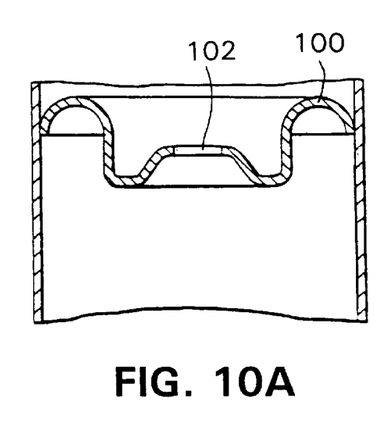
FIGS. 10(a) and 10(b) illustrate modifications of the insert in the dispersion chamber.
Figure 10B:
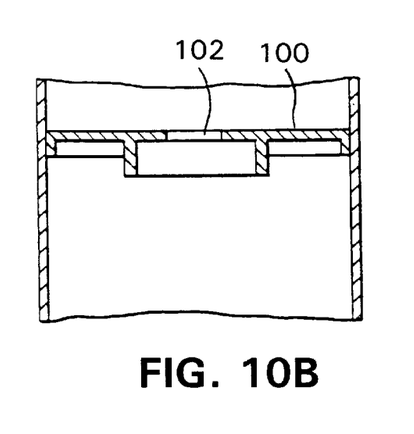
Figure 11A:
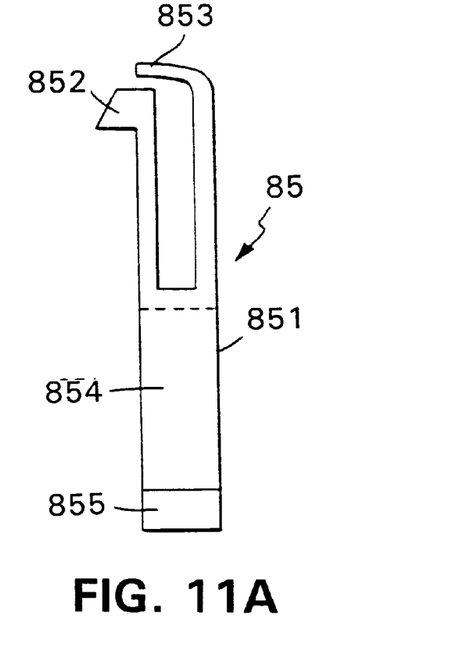
FIGS. 11(a) to 11(d) illustrate the component parts of the knocker assembly of the device of FIG. 1.
Figure 11B:
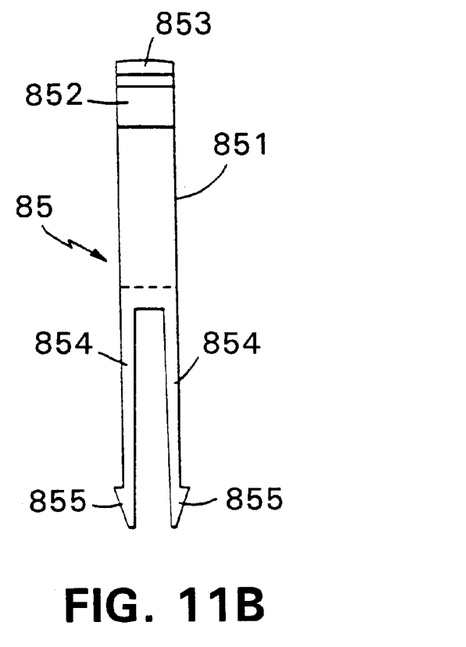
Figure 11C:
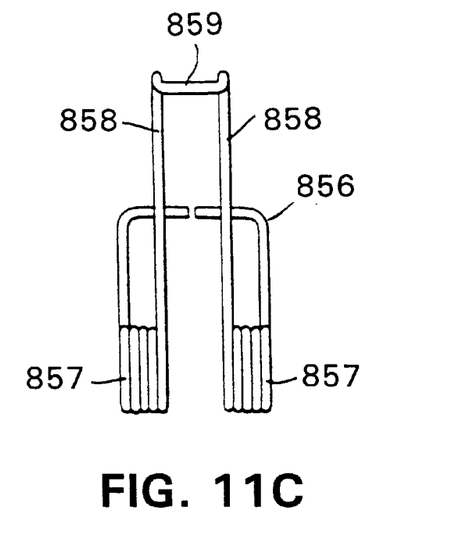
Figure 11D:
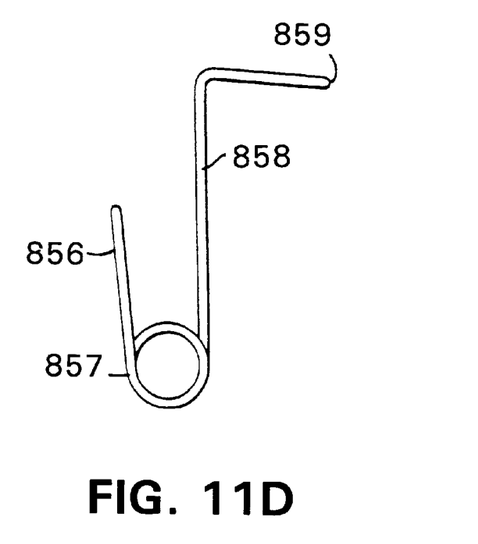

In a preferred embodiment, as illustrated in FIG. 9, an insert 100 can be provided in the dispersion chamber 3 in order to provide a peripheral channel for preventing powder which has collected in the bottom of the dispersion chamber 3 from escaping from the dispersion chamber 3 into the inhalation channel 33 of the lid 31 or into the mouthpiece 32. Preferably, the insert 100 is frusto-conical in shape with smaller opening thereof being directed downwards towards the bottom wall 35 of the dispersion chamber 3. However, any form which provides a peripheral channel around an outlet 102 could be employed, such as a curved cross section as illustrated in FIG. 10(a) and a ridged cross section as illustrated in FIG. 10(b).

As described hereinabove, in use, powder is drawn out of the inhaler 7, through the channel 8 and into the dispersion chamber 3. It can happen that substance which has been drawn out of the inhaler 7 settles on surfaces of the channel 8. In order to reduce this effect, the device further comprises a knocker assembly 85 which knocks the wall of the channel 8 prior to each use of the device, such that any previously deposited powder is dislodged from an inner surface of the channel 8 by virtue of the vibrations created in the wall.

The component parts of the knocker assembly 85 are illustrated in greater detail in FIGS. 11(a) to 11(d). The knocker assembly comprises a hook member 851 which includes a hook element 852 that fits into the outlet opening of the mouthpiece 32 as illustrated in FIG. 1. The hook member 851 further includes a lip 853 which in use is disposed in the gap between the end of the mouthpiece 32 and the housing 1 opposite. The lower section of the hook member 851 includes two legs 854 each of which include projections 855 that engage a spring 856. The knocker assembly 85 further comprises a spring 856 which comprises two coils 857 that are joined by two generally parallel extensions 858 and a knocker element 859.

Figure 2:
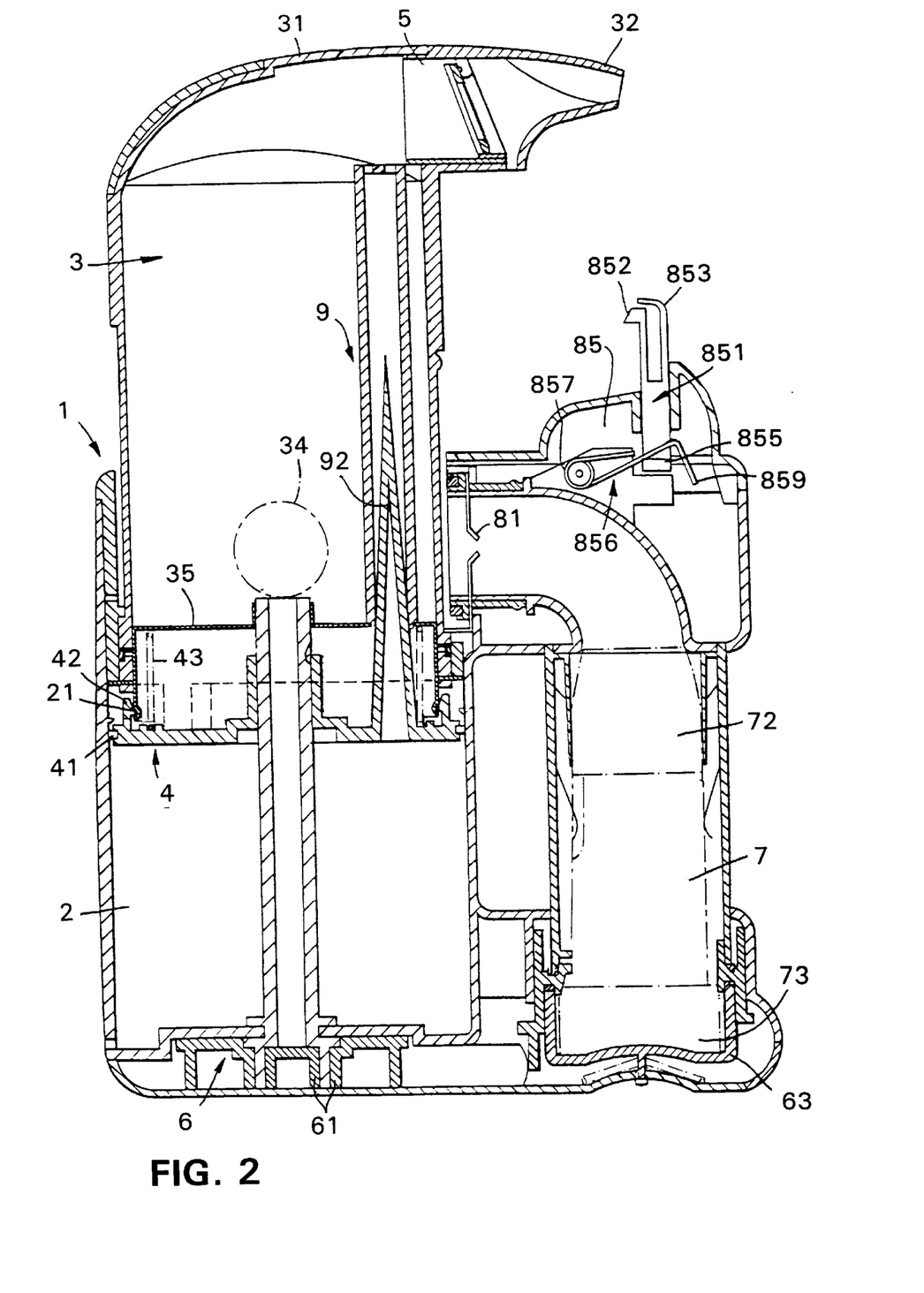

As illustrated in FIG. 1, in the storage position, the hook member 851 is positioned with the hook 852 in the opening of the mouthpiece 32 and the legs 854 between the extensions 858 of the spring 856. When the dispersion chamber 3 is telescopically extended from the housing 1, the hook 852 which is engaged in the opening of the mouthpiece 32 causes the hook member 851 to be pulled up out of the housing 1. The projections 855 then engage the extensions 858 of the spring 856 and deflect the same upwardly against the resilient resistance of the spring 856. Thus, the knocker assembly 85 is moved to the position illustrated in FIG. 2, though of course, it will not remain in this position due to the resilience of the spring 856. In fact, once the knocker assembly 85 reaches the position illustrated in FIG. 2, either the resilient resistance of the spring 856 or the physical engagement of the knocker assembly 85 with a stop in the housing 1 prevents the knocker assembly 85 from moving any further. At this point, the hook 852 is deflected out of the opening of the mouthpiece 32, thereby releasing the knocker assembly 85 such that the spring 856 relaxes and drives the knocker 859 against the outer surface of wall of the channel 8 as illustrated in FIG. 3. As described hereinabove, this impact dislodges any powder which may have deposited on internal surfaces of the channel 8.

The hook member 851 may also be configured to operate in a slightly different manner. In particular, if the resilience of the spring 856 is chosen appropriately or a detent is provided or the spring 856, the legs 854 may deflect inwardly, releasing the projections 855 from the extensions 858 of the spring 856 before the hook 852 releases from the opening of the mouthpiece 32. In this case, the knocker 859 will hit the outer surface of the wall of the channel 8 in the same manner as described hereinabove. Subsequently, when the mouthpiece 32 is returned to the storage position, it will push the hook member 851 down onto the spring 856, deflecting the legs 854 such that the projections 855 once again engage between the extensions 858 of the spring 856.

Finally, it will be understood by a person skilled in the art that the present invention has been described in its preferred embodiment and can be modified in many different ways without departing from the scope of the invention as defined in the appended claims.

What is claimed is:

1. A spacer for connection to an inhaler and providing a substance in a dispersed state, comprising:

a plurality of internal surfaces for ducting and containing the substance in the dispersed state;

an outlet including an opening through which the substance is in use inhaled;

a vibrator for creating vibrations in at least one of the internal surfaces for as to prevent accumulation of substance thereon; and a component movable between a first position and a second position, the component being mechanically linked to the vibrator so as to actuate the vibrator and create vibrations in the at least one of the internal surfaces when the component is moved between the first and second positions.

2. The spacer according to claim 1, wherein the outlet comprises a mouthpiece.

3. The spacer according to claim 1, configured so as to be inoperable with the component in the first position and operable with the component in the second position.

4. A spacer for connection to an inhaler and providing a substance in a dispersed state, comprising:

a plurality of internal surfaces for ducting and containing the substance in the dispersed state;

an outlet including an opening through which the substance is in use inhaled;

a vibrator for creating vibrations in at least one of the internal surfaces so as to prevent accumulation of substance thereon; and a component movable between a first position and a second position, the component being linked to the vibrator so as to actuate the vibrator and create vibrations in the at least one of the internal surfaces when the component is moved between the first and second positions, wherein the component includes the outlet.

5. A spacer for connection to an inhaler and providing a substance in a dispersed state, comprising:

a plurality of internal surfaces for ducting and containing the substance in the dispersed state;

an outlet including an opening through which the substance is in use inhaled;

a vibrator for creating vibrations in at least one of the internal surfaces so as to prevent accumulation of substance thereon; and a component movable between a first position and a second position, the component being linked to the vibrator so as to actuate the vibrator and create vibrations in the at least one of the internal surfaces when the component is moved between the first and second positions, further comprising a wall member in mechanical connection with the at least one of the internal surfaces, wherein the vibrator comprises a contact element disposed adjacent the wall member and a resilient element for biasing the contact element towards the wall member.

6. The spacer according to claim 5, wherein the contact element is configured so as to be movable by the component against the bias of the resilient element when the component is moved between the first and second positions and released such as to be driven by the resilient element to impact the wall member and create vibrations in the at least one of the internal surfaces.

7. The spacer according to claim 6, wherein the vibrator comprises a hook member which is coupled to the resilient element.

8. The spacer according to claim 7, wherein the hook member includes a hook element which engages the opening of the outlet when the component is moved between the first and second positions.

9. The spacer according to claim 5, wherein the internal surfaces define a chamber for containing the substance in a dispersed state.

10. The spacer according to claim 9, wherein the internal surfaces further define a channel for ducting the substance to the chamber, with the wall member being connected to at least one of the internal surfaces defining the channel.

11. The spacer according to claim 5, wherein the resilient element comprises a spring.

12. A combination comprising:

an inhaler having an inhalation channel; reservoir containing a substance to be inhaled, and an inhaler outlet for passage of said substance in a dispersed state and entrained in air flowing through said inhalation channel, a spacer inlet having structure for making a fluid connection to said inhaler outlet, a plurality of internal surfaces for ducting and containing the substance in the dispersed state;

a spacer outlet including an opening through which the substance is in use inhaled;

a vibrator or creating vibrations in at least one of the internal surfaces so as to prevent accumulation of substance thereon; and a component movable between a first position and a second position, the component being mechanically linked to the vibrator so as to actuate the vibrator and create vibrations in the at least one of the internal surfaces when the component is moved between the first and second positions.

13. The combination according to claim 12, wherein the spacer outlet comprises a mouthpiece.

14. The combination according to claim 12, configured so as to be inoperable with the component in the first position and operable with the component in the second position.

15. A combination comprising:

an inhaler having an inhalation channel, a reservoir containing a substance to be inhaled, and an inhaler outlet for passage of said substance in a dispersed state and entrained in air flowing through said inhalation channel, a spacer comprising;

a spacer inlet having structure for making a fluid connection to said inhaler outlet, a plurality of internal surfaces for ducting and containing the substance in the dispersed state;

a spacer outlet including an opening through which the substance is in use inhaled;

a vibrator for creating vibrations in at least one of the internal surfaces so as to prevent accumulation of substance thereon; and a component movable between a first position and a second position, the component being linked to the vibrator so as to actuate the vibrator and create vibrations in the at least one of the internal surfaces when the component is moved between the first and second positions, wherein the component includes the spacer outlet.

16. A combination comprising:

an inhaler having an inhalation channel, a reservoir containing a substance to be inhaled, and an inhaler outlet for passage of said substance in a dispersed state and entrained in air flowing through said inhalation channel, a spacer comprising;

a spacer inlet having structure for making a fluid connection to said inhaler outlet, a plurality of internal surfaces for ducting and containing the substance in the dispersed state;

a spacer outlet including an opening through which the substance is in use inhaled;

a vibrator for creating vibrations in at least one of the internal surfaces so as to prevent accumulation of substance thereon; and a component movable between a first position and a second position, the component being linked to the vibrator so as to actuate the vibrator and create vibrations in the at least one of the internal surfaces when the component is moved between the first and second positions, further comprising a wall member in mechanical connection with the at least one of the internal surfaces, wherein the vibrator comprises a contact element disposed adjacent the wall member and a resilient element for biasing the contact element towards the wall member.

17. The combination according to claim 16, wherein the contact element is configured so as to be movable by the component against the bias of the resilient element when the component is moved between the first and second positions and released such as to be driven by the resilient element to impact the wall member and create vibrations in the at least one of the internal surfaces.

18. The combination according to claim 17, wherein the vibrator comprises a hook member which is coupled to the resilient element.

19. The combination according to claim 18, wherein the hook member includes a hook element which engages the opening of the spacer outlet when the component is moved between the first and second positions.

20. The combination according to claim 16, wherein the internal surfaces define a chamber for containing the substance in a dispersed state.

21. The combination according to claim 20, wherein the internal surfaces further define a channel for ducting the substance to the chamber, with the wall member being connected to at least one of the internal surfaces defining the channel.

22. The combination according to claim 16, wherein the resilient element comprises a spring.

* * * * *